(12) United States Patent
Ekey

(10) Patent No.: US 6,461,319 B1
(45) Date of Patent: Oct. 8, 2002

(54) COMFORT SUPPORT SYSTEM FOR MEDICINAL AND THERAPEUTIC DEVICES

(76) Inventor: Barbara N. Ekey, c/o 393 Keller Rd., Warren, PA (US) 16365

(*) Notice: Subject to any disclaimer, the term of this patent is extended or adjusted under 35 U.S.C. 154(b) by 0 days.

(21) Appl. No.: 09/774,979

(22) Filed: Jan. 31, 2001

(51) Int. Cl.[7] .............................................. A61F 13/00
(52) U.S. Cl. ..................... 602/62; 604/93.01; 604/174; 604/179
(58) Field of Search ................................ 604/345, 179, 604/327, 353, 93.01, 174, 332; 224/682, 663, 676; 602/60–62

(56) References Cited

U.S. PATENT DOCUMENTS

| | | | |
|---|---|---|---|
| 1,968,767 A | 7/1934 | Howard | 221/23 |
| D128,066 S | 7/1941 | Haubein | |
| 2,699,782 A | 1/1955 | Chester | 128/295 |
| 2,900,979 A | 8/1959 | Bishop | 128/283 |
| D277,810 S | 3/1985 | Pickens | D2/383 |
| 4,504,267 A | * 3/1985 | Parmelee et al. | 604/134 |
| 4,511,358 A | * 4/1985 | Johnson, Jr. et al. | 604/327 |
| 4,548,375 A | 10/1985 | Moss | 248/205.2 |
| 4,819,846 A | 4/1989 | Hannemann | 224/240 |
| 4,923,105 A | 5/1990 | Snyder | 224/255 |
| 5,026,362 A | 6/1991 | Willett | 604/345 |
| 5,032,118 A | 7/1991 | Mason | 604/349 |
| D319,732 S | 9/1991 | Gumbs | D3/100 |
| 5,087,251 A | 2/1992 | Heyman et al. | 604/327 |
| 5,135,519 A | 8/1992 | Helmer | 604/332 |
| 5,193,553 A | * 3/1993 | Kalinoski | 128/767 |
| 5,259,541 A | 11/1993 | Reese | 224/226 |
| D365,928 S | 1/1996 | Sauer | D3/224 |
| 5,643,233 A | 7/1997 | Turner | 604/332 |
| 5,651,777 A | 7/1997 | Walters | 604/345 |
| 5,980,499 A | 11/1999 | Ekey | 604/345 |

* cited by examiner

Primary Examiner—Michael A. Brown
Assistant Examiner—Lalita M. Hamilton
(74) Attorney, Agent, or Firm—Thompson Hine LLP

(57) ABSTRACT

A medical apparatus support system including a pouch assembly for comfortably and effectively supporting a medical device, such as an intravenous supply bag. The pouch assembly including an opening to receive the supply bag in a pocket and a slit to allow egress of a supply tube associated with the supply bag positioned near the lower portion of the pocket, wherein the pouch assembly further includes an extension extending from a position proximal the slit.

15 Claims, 3 Drawing Sheets

COMFORT SUPPORT SYSTEM FOR MEDICINAL AND THERAPEUTIC DEVICES

BACKGROUND OF THE INVENTION

This invention relates to medicinal and therapeutic supports, and more particularly to comfortable supports to be worn about the body, namely the shoulders, abdomen, thorax, upper thigh or head, for antibiotic and other types of medicinal delivery systems, drainage receptacles, and medical diagnostic and monitoring equipment.

Often in the treatment of medical patients it may be required to provide continuous intravenous medicines to the patient, such as antibiotics, continuously. Often times, these intravenous medicines may be required even after the patient's hospital stays are over. Additionally, sometimes patients require diagnostic or monitoring equipment that need to be attached to or in close proximity to the body most of the time. Most of the aforementioned apparatuses are attached to the body of the patient at various insertion points by intravenous tubes, electrical sensors, drainage tubes, etc., hereinafter generally referred to as "lines." Traditionally, these apparatuses have been required to be supported by a "johnny pole" including a support hook at one end and wheels at the other so that the patient can drag along the pole and attached medical apparatuses with them wherever they go. Needless to say this arrangement can be awkward and inconvenient for the patient, and sometimes can result in longer than necessary hospital stays.

For this reason it is generally preferred that these apparatuses be attached and supported on the body of the patient so that the need for the awkward and unwieldy "johnny pole" can be eliminated. Furthermore, if at all possible, it is desired that the medical apparatus be supported at or close to the insertion point of the medicinal intravenous tubes, the diagnostic apparatus sensor, the drainage tubes, etc. in order to limit the possibility of the tangling or interferences of the lines as they are usually held in place delicately. Additionally, entanglement with the wearer, the wearer's clothes, etc., is also an undesirable condition that should be avoided.

In the past, in a somewhat unsuccessful attempt to eliminate the need for a johnny pole, it was common to pin or tape the medical apparatuses to clothing worn by the patient or to the bandage or the incision itself. While not very comfortable, this procedure was somewhat effective in helping out the patient, especially while the patient was in the hospital where an open gown was worn, thereby easing the ability of the patient to accommodate basic bodily functions. However, the awkwardness and discomfort is increased with multiple sets of apparatuses and the related lines. In addition, outside the hospital, where patients wear standard, relatively constricting clothes, it is not practicable to use the prior art pinning and taping methods to support the apparatuses. As mentioned above, other problems arise from the entanglement of the lines. For example, these lines are generally connected to the apparatuses with an ample amount of "slack" so that they will be usable in varying applications by patients of differing sizes and shapes. However, the extra length of the lines can become easily entangled with the wearer, the wearer's clothing, etc., especially when several apparatuses are being used. While several attempts have been in the past to resolve some of these noted problems, these attempts have achieved only moderate success.

For example, U.S. Pat. No. 5,643,233 to Turner attempts to address some of these problems specifically with respect to drainage receptacles providing a single large pouch to be worn on a belt which extends about the waist of a post operative patient to support a fluid drainage receptacle. The pouch of that device includes a pouch extension and an elongated loop of fabric which receives the belt and supports the pouch so that the pouch opening hangs down below the belt and deflects in an angular position when the lip of the pouch is pulled away from the wearer, thereby allowing easy access to the interior of the pouch.

While the Turner patent resolves some of the problems associated specifically with prior art post operative drainage receptacle supports, it is not generally effective for other devices. Specifically, while the apparatus disclosed in the Turner patent is acceptable for some drainage receptacle support situations, it is generally ineffective for supporting an intravenous medicinal supply. This particularly true if the insertion point of the intravenous line is above the waist of the patient.

Accordingly, there exists a need for a lightweight support device for medical apparatuses to be worn by post operative patients which comfortably secures the apparatuses against a wearer, a support device which eliminates the prior art need for an unwieldy support device such as a johnny pole, a support device which can be worn under clothing, a support device which facilitates the operation of the apparatuses, a support device which prevents line entanglements, a support device which holds the apparatuses in a desired, operational position, a support device which may be used with apparatuses of varying sizes and shapes, a support device that can be positioned above the insertion point of an intravenous line, and a support device which can be positioned in a manner to avoid tangling and stress on the related apparatus lines.

SUMMARY OF THE INVENTION

The present invention is a medical apparatus support system which may be used to securely support a number of medical apparatuses, including medicinal delivery systems, drainage receptacles, and medical diagnostic and monitoring equipment and the like, and can be worn comfortably on the body of a medical patient such that the need for an unwieldy support device such as a johnny pole is eliminated. In a preferred embodiment, the present invention provides an intravenous medicinal support device that can be worn on the shoulder of a patient above the insertion point of the intravenous line in order to provide gravitational assistance to the flow of the medicine. In all embodiments, the present invention includes at least one adjustable belt and at least one pouch shaped to receive a medical apparatus. For one preferred embodiment disclosed herein, a shoulder belt and specially adapted pouch including a feature to help insure the operational positioning and security of an intravenous supply bag or other medical apparatus in the pouch is provided. In a preferred embodiment, a pouch extension and arm straps are included to provide further support for the medicine supply bag and the intravenous drip reservoir. Of course the pouches for holding the apparatuses in accordance with the present invention may be constructed in many different ways, and can include a side panel or gusset so that the pouches may comfortably receive larger sized apparatuses. Preferably, the pouches and other supports of the present invention are made from a lightweight, non-abrasive, washable fabric having padding positioned between the apparatus and the body of the wearer.

In a preferred embodiment of the present invention, a flap of fabric or other suitable material is affixed near the exit point of the intravenous bag, preferably on a pocket extension, to support an auxiliary device, such as an intravenous drip reservoir. The flap is secured to the pocket extension to form a hinge and includes one element of a releasable closure, such as a snap, a button, strips of hook and loop material or the like, affixed to the free end of the "hinge." The other element of the releasable closure is then affixed to one side of the pouch extension thereby enabling the flap to form a loop when the flap is releasably fastened to the other side of the pouch extension. The loop can then be used to support the intravenous drip reservoir, thereby preventing the reservoir from putting stress on the medicinal supply bag. Similarly, the loop can be used to secure excess slack from the intravenous line tube or diagnostic line from a diagnostic apparatus, thereby lessening the possibility that the lines will become entangled with the wearer, door handles of other objects.

Accordingly, it is an objective of the present invention to provide a medical apparatus support system which may be used to securely support a number of medical apparatuses, including medicinal delivery systems, drainage receptacles, and medical diagnostic and monitoring equipment and the like, that can be worn comfortably on the body of a medical patient. Other objects and advantages of the present invention will be apparent from the following description, the accompanying drawing and the appended claims.

DETAILED DESCRIPTION

Figure 1:
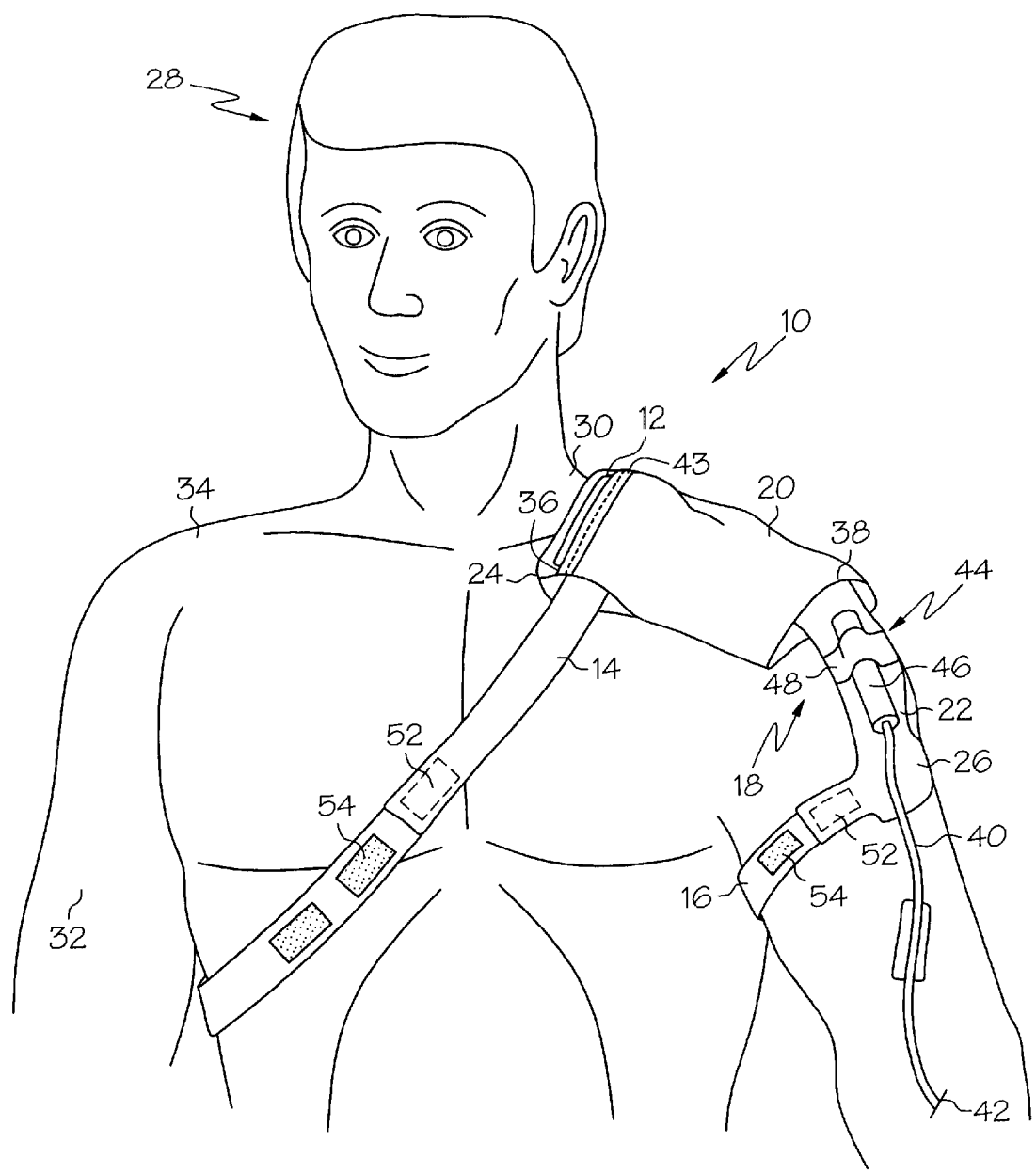
FIG. 1 is a front perspective view of a preferred embodiment of a medicinal and therapeutic apparatus support system of the present invention, shown worn by a postoperative patient.

As best shown in FIG. 1, in accordance with a preferred embodiment of the present invention, a support system, generally designated 10, for a medicinal or therapeutic apparatus, preferably a medicinal delivery system such as a medicinal bag 12, includes a primary adjustable shoulder belt 14, at least one secondary adjustable upper arm belt 16, and a pouch assembly 18. The pouch 18 assembly preferably comprises a pocket 20, a pouch extension 22, and at least two belt loops 24, 26. The primary adjustable shoulder belt 14 is shaped to be worn around the abdomen, thorax, head or upper thigh of a patient 28, but preferably is shaped to be worn over one shoulder 30 of the patient and underneath the arm 32 attached to the opposite shoulder 34. While a human patient 28 is shown in FIG. 1, the system 10 may be employed on animals, such as horses and cows as well, and therefore are to be included with the term "patient" as used herein. Additionally, while the preferred embodiment of the invention shown herein is shown as worn by a patient 28 over the shoulder of the patient 28, one of ordinary skill will see that the primary belt 14 could be worn around the waist of a patient and the secondary belt 16, 16B could be worn about the upper thigh of a patient 28 to provide support for a medical apparatus having a line 40 insertion point below the waist of the patient 28.

The pouch assembly 18 includes at least two belt loops 24, 26 shaped to slidably receive a primary adjustable shoulder belt 14, and at least one secondary adjustable upper arm belt 16, and an includes a pocket 20 to receive an individual medicinal or therapeutic apparatus, such as a medicinal bag 12. Preferably, the pocket 20 includes an upper opening 36 and a lower slit 38. The upper opening 36 is sized to easily receive the medicinal or therapeutic apparatus 12. The lower slit 38 is sized to allow the line 40, such as an intravenous supply tube, from the apparatus 12 to exit the pocket 20 while still providing adequate support to the apparatus 12. The line 40 then may be fed to the incision or insertion point 42 of the line 40 on the patient 28.

Preferably the pouch assembly 18 includes a feature to help ensure that the apparatus, such as a medicinal bag 12, is held securely in the pocket 20 in a desired operational position. As shown best in FIG. 2, this feature can be an elastic strip 43 that encircles the upper opening of the pocket 20 to secure the bag 12 in the pocket. As shown best in FIG. 3, this feature can be additional padding 45 that is placed between the pocket 20 and lower portion of the pouch assembly 18. Preferably this padding 45 is positioned proximal the upper opening 36 and operates to bias the bag 12 toward the lower slit 38. In this manner, as intravenous liquid is drained from the bag 12, complete draining of the bag 12 to the patient 28 is facilitated. Additionally, the padding 45 operates to help secure the bag 12 in the pocket 20.

Preferably, the pouch assembly 18 also includes a pouch extension 22 with a releasable support loop 44 positioned thereon to provide additional support for the line 40 or another auxiliary device, such as an intravenous drip reservoir 46. The support loop 44 is preferably comprised of a flap of fabric 48 or other suitable material that is affixed near the slit 38 on the pouch extension 22. The flap 48 is secured to the pouch extension 22 to form a hinge and includes one element of a releasable closure, such as a snap, a button, strips of hook and loop material or the like, affixed to the free end of the "hinge." The other element of the releasable closure is then affixed to one side of the pouch extension 22 thereby enabling the flap 48 to form the support loop 44 when the flap 48 is releasably fastened to the other side of the pouch extension 22. The loop 44 can then be used to support the intravenous drip reservoir 46, thereby preventing the reservoir from putting stress on the apparatus 12. Similarly, the loop 44 can be used to secure excess slack from the line 40 thereby lessening the possibility that the line 40 will become entangled with the wearer, door handles of other objects.

Figure 2:
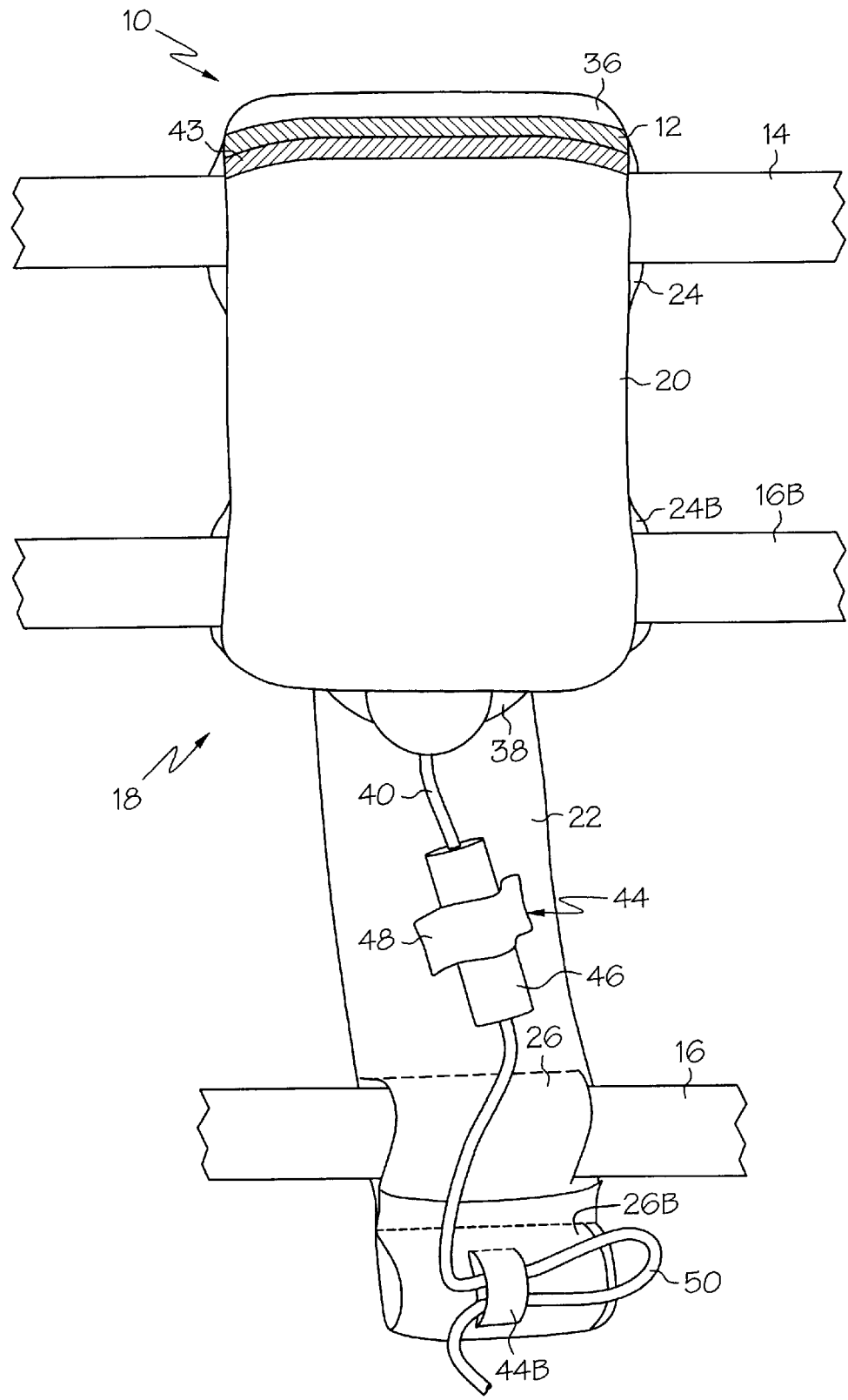
FIG. 2 is a front plan view of the belt of an alternate embodiment of the support system of FIG. 1.
Figure 3:
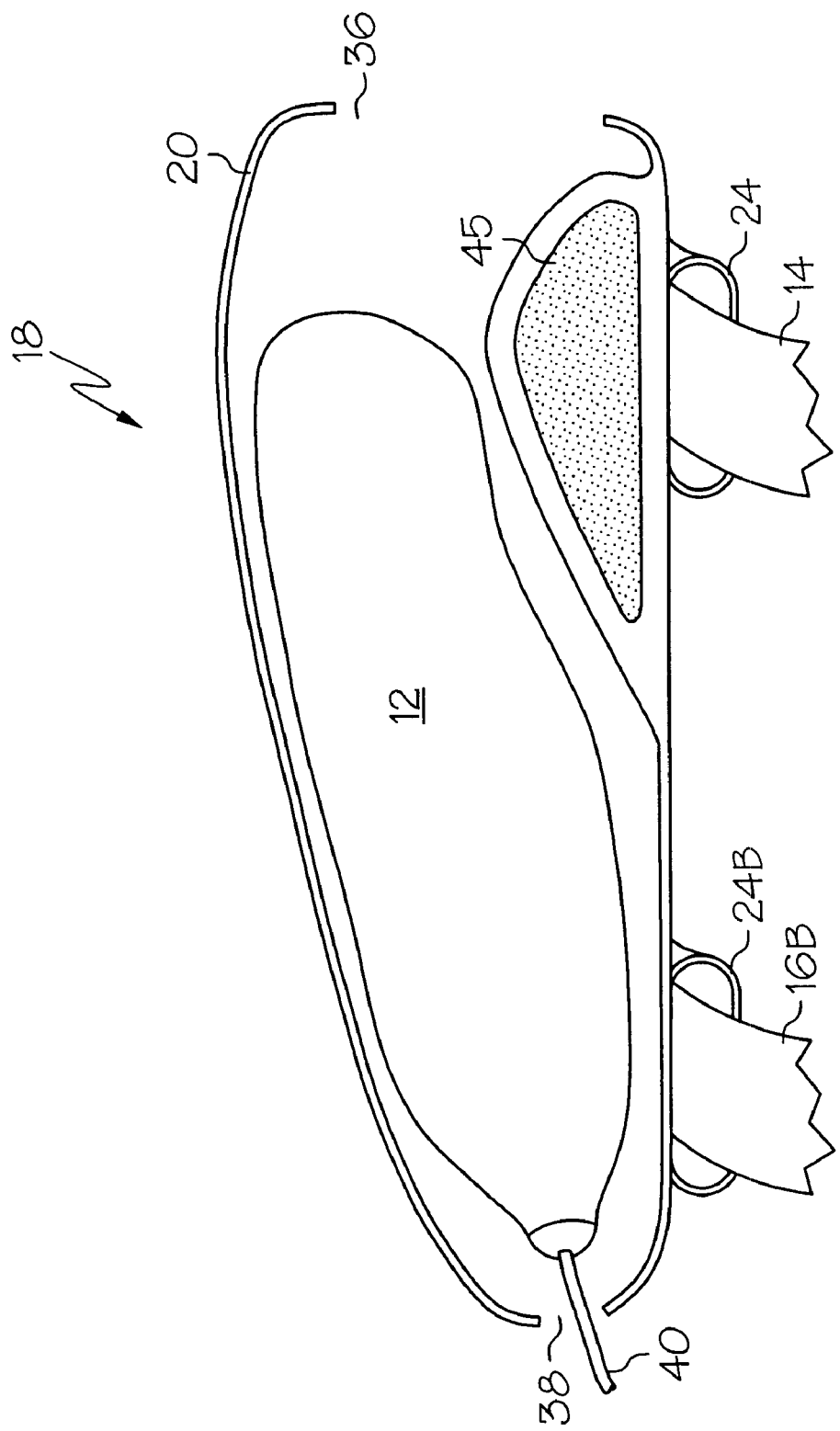
FIG. 3 is a partial cutaway side elevational view of an embodiment of a pouch for use in the medicinal and therapeutic support system of FIG. 1.

As shown best in FIG. 2, changes and additions to the embodiment of the invention shown in FIG. 1 are possible without departing from the overall scope of the present invention. More specifically, in a preferred embodiment, another secondary adjustable upper arm belt 16B, and corresponding belt loop 24B is provided with the pouch assembly 18 to provide additional support to the apparatus 12. Additionally, the pouch extension 22 may include another belt loop 26B for providing the opportunity to further adjust the support provided to the apparatus 12. Furthermore, the pouch extension 22 may also include an additional line support loop 44B constructed similarly to the support loop 44 to provide the ability to collect excess slack in the form of a bundle 50 from the line 40. These additional features provide the patient 28 with the ability to adjust the support system 10 of the present invention to provide as much comfort and support as possible. Of course, one of ordinary skill in the art would understand that these same features may be added several more times to provide even more adjustment ability and it is to be understood that such modifications are considered within the scope of the present invention.

In all of the embodiments of the present invention, the adjustable belts 14, 16, 16B may be made of any suitable material and construction but are preferably made from an elastic fabric material that has a non-abrasive facing attached to the inside portion facing the patient 28. The adjustment ability of the belts 14, 16, 16B may be accomplished using any suitable method but is preferably accomplished by attaching hook material 52 to the inside of the free end of the belts 14, 16, 16B and spacing complementary strips of loop material 54 around the outside of the belts 14, 16, 16B spaced a distance apart from each other.

The pouch assembly 18 and pocket of the present invention may also be made of any suitable material and construction but is preferably made from a soft, non-abrasive material such as cotton material preferably including a padding material incorporated therein.

A preferred method of operation of the support system 10 of the present invention is as follows. The primary adjustable shoulder belt 14 is placed through belt loop 24 and over the shoulder 30 of the patient 28. The belt 14 is then fed under the arm 32 of the patient 28 and secured snugly using the hook 52 and loop 54 material. The pouch assembly 18 is then positioned on the shoulder 30 of patient 28. Next, the secondary adjustable arm belts 16, 16B are similarly threaded through their respective belt loops 26 or 26B, 24B and secured around the upper arm of the patient 28 such that the pouch extension 22 extends downwardly along the arm of the patient 28. The medical apparatus, such as a medicinal supply bag 12, is then placed through the opening 36 into the pocket 20 such that is supported in a downward position with any associated lines, such as an intravenous supply line 40, extending through the slit 38. If an intravenous drip reservoir 46 is used, it can be secured to the pouch extension 22 using the support loop 44. Furthermore, any excess slack from the intravenous line 40 is collected and folded upon itself to form a bundle 50. The bundle 50 is then held securely in place using the support loop 44B.

While the form of the apparatus therein described constitutes a preferred embodiment of the invention, it is to be understood that the invention is not limited to the precise form of apparatus, and that changes may be made therein without departing from the scope of the invention.

What is claimed is:

1. A support system for an intravenous supply bag comprising:
   at least one primary adjustable belt shaped to be worn about the shoulder, abdomen, thorax, or waist of a patient;
   at least one secondary adjustable belt shaped to be worn about the arm or the leg of a patient;
   a pouch assembly having a front and a back including a pocket having an intravenous supply bag therein, said pocket having an upper portion and a lower portion, said pocket including an opening to receive said medical apparatus in said pocket positioned near said upper portion of said pocket and a slit to allow egress of a line associated with said intravenous supply bag positioned near said lower portion of said pocket, said pouch assembly further including an extension connected to and extending from said pocket assembly lower portion;
   at least one primary belt loop attached to said pouch assembly, said primary belt loop shaped to receive said primary adjustable belt;
   at least one secondary belt loop attached to said pouch assembly, said secondary belt loop shaped to receive said secondary adjustable belt;
   wherein said pouch assembly supports said intravenous supply bag in a secure and operable against said patient.

2. The support system of claim 1 further comprising an intravenous drip reservoir connected to said intravenous supply bag and at least one support loop attached to said extension for securing said intravenous drip reservoir.

3. The support system of claim 2 wherein said support loop comprises a flap of fabric having a free end with one element of a releasable closure attached thereto, an end that is affixed to said extension, and a complementary element of said releasable closure attached to said extension such that said flap of fabric may be releasably attached to said extension to support said intravenous drip reservoir between said flap of fabric and said extension.

4. The support system of claim 3 wherein said releasable closure is selected from the group consisting of hook and loop material, snaps, buttons, and clasps.

5. The support system of claim 1 further comprising at least two support loops attached to said pouch assembly.

6. The support system of claim 5 wherein one of said support loops is positioned proximal said slit in a horizontal orientation with respect to said extension and is shaped to hold an intravenous drip reservoir.

7. The support system of claim 5 wherein one of said support loops is positioned in a vertical orientation with respect to said extension and is shaped to hold a bundle of said line attached to said apparatus.

8. The support system of claim 1 wherein said primary belt loop is attached to said back of said pouch assembly proximal said opening, one of said secondary belt loops is attached to said back of said pouch assembly proximal said slit, and another of said secondary belt loops is attached to said extension.

9. The support system of claim 8 including two secondary belt loops attached to said extension.

10. The support system of claim 1 wherein said pouch assembly is made of a relatively non-abrasive material and having padding incorporated therein.

11. The support system of claim 1 including padding positioned in said upper portion of said pocket to bias said intravenous supply bag positioned in said pocket towards said slit.

12. The support system of claim 1 including an elastic material positioned proximal said opening to aid in securing said intravenous supply bag within said pocket.

13. A support system for an intravenous supply bag comprising:
   one primary adjustable belt shaped to be worn about the shoulder of a patient;
   two secondary adjustable belts shaped to be worn about the arm of a patient;
   a pouch assembly having a front and a back including a pocket having an intravenous supply bag placed therein and including an intravenous drip reservoir connected thereto, said pocket having an upper portion and a lower portion, said pocket including an opening to receive said supply bag in said pocket positioned near said upper portion of said pocket and a slit to allow egress of a supply tube associated with said supply bag positioned near said lower portion of said pocket, said pouch assembly further including an extension extending from a position proximal said pouch assembly lower portion;
   one primary belt loop attached to said pouch assembly, said primary belt loop shaped to receive said primary adjustable belt;
   at least two secondary belt loops attached to said pouch assembly, said secondary belt loops shaped to receive said secondary adjustable belts;

at least one support loop attached to said extension said support loop comprising a flap of fabric having a free end with one element of a releasable closure attached thereto, an end that is affixed to said extension, and a complementary element of said releasable closure attached to said extension such that said flap of fabric may be releasably attached to said extension to support said intravenous drip reservoir between said flap of fabric and said extension;

padding positioned in said pouch assembly proximal said opening to bias said supply bag towards said slit;

wherein said pouch assembly supports said supply bag in a secure and operable against said patient.

14. A method for supporting an intravenous supply bag connected to a medical patient comprising:

selecting a primary adjustable belt shaped to be worn about the shoulder of a patient;

selecting two secondary adjustable belts shaped to be worn about the arm of a patient;

selecting a pouch assembly having a front and a back including a pocket shaped to receive an intravenous supply bag, said pocket having an upper portion and a lower portion, said pocket including an opening to receive said supply bag in said pocket positioned near said upper portion of said pocket and a slit to allow egress of a supply tube associated with said supply bag positioned near said lower portion of said pocket, said pouch assembly further including an extension extending from a position proximal said pocket lower portion;

said pouch assembly including one primary belt loop attached to said pouch assembly, said primary belt loop shaped to receive said primary adjustable belt, at least two secondary belt loops attached to said pouch assembly, said secondary belt loops shaped to receive said secondary adjustable belts;

inserting said primary belt through said primary belt loop and around the shoulder of said patient;

adjusting said primary belt to a desired length;

inserting said secondary belts through said secondary belt loops;

adjusting said secondary belts to a desired length;

inserting an intravenous supply bag in said pocket while feeding an associated line through said slit to an insertion point on said patient such that said supply bag is supported on a shoulder of said patient above an insertion point of an intravenous line in order to provide gravitational assistance to the flow of medicine from said intravenous supply bag.

15. The method of claim 14 further comprising the step of selecting a pouch assembly having at least one support loop attached to said extension for securing an intravenous drip reservoir.

* * * * *